(12) United States Patent
McLain et al.

(10) Patent No.: US 9,724,112 B2
(45) Date of Patent: Aug. 8, 2017

(54) SHAPE MEMORY METAL EMBOLI TRAP

(71) Applicant: COOK MEDICAL TECHNOLOGIES LLC, Bloomington, IN (US)

(72) Inventors: Cameron McLain, Columbus, OH (US); Connor Cunnane, Bloomington, IN (US); Marie Hopkins, Cleveland, OH (US); Brian Gaerke, Coldwater, OH (US); Clay Sudlow, Van Buren, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 248 days.

(21) Appl. No.: 14/199,447

(22) Filed: Mar. 6, 2014

(65) Prior Publication Data

US 2014/0276922 A1 Sep. 18, 2014

Related U.S. Application Data

(60) Provisional application No. 61/788,549, filed on Mar. 15, 2013.

(51) Int. Cl.
*A61M 29/00* (2006.01)
*A61B 17/221* (2006.01)
(Continued)

(52) U.S. Cl.
CPC ........ *A61B 17/221* (2013.01); *A61B 17/3207* (2013.01); *A61F 2/013* (2013.01);
(Continued)

(58) Field of Classification Search
CPC .............. A61B 17/221; A61B 17/3207; A61B 2017/22044; A61B 2017/22094; A61B 17/22031; A61B 17/320725; A61B 17/32075; A61B 2017/22034; A61B 2017/22035; A61B 2017/320716; A61B 2017/320741; A61F 2/013; A61F 2/01; A61F 2002/011; A61F 2002/015; A61F 2002/016; A61F 2002/018
(Continued)

(56) References Cited

U.S. PATENT DOCUMENTS 3,108,593 A 10/1963 Glassman
3,334,629 A 8/1967 Cohn
(Continued)

*Primary Examiner* — Jonathan Miles
*Assistant Examiner* — Kankindi Rwego
(74) *Attorney, Agent, or Firm* — Brinks Gilson & Lione

(57) ABSTRACT

An embolus trap device is provided. The embolus trap device consists of an outer catheter, an inner catheter, a plurality of filter baskets, and a plurality of basket collapse wires. The filter baskets are of different radius and are positioned along the inner catheter in order of increasing radius from the proximal to the distal end. The filter baskets increase in radius so that any embolic fragment that flows past each basket has a chance to be caught and secured by a filter basket distal to it. The filter baskets are separately collapsible by the plurality of collapse wires and are collapsed in proximal-to-distal fashion with the largest basket being closed last in order to capture embolic fragments that may emerge from the smaller baskets because of disruptions as they are closed.

17 Claims, 6 Drawing Sheets

(51) Int. Cl.
  *A61B 17/3207*  (2006.01)
  *A61F 2/01*  (2006.01)
  *A61B 17/22*  (2006.01)

(52) U.S. Cl.
  CPC .............. *A61B 2017/2212* (2013.01); *A61B 2017/22044* (2013.01); *A61B 2017/22094* (2013.01); *A61F 2002/016* (2013.01)

(58) Field of Classification Search
  USPC ........................................................ 606/200
  See application file for complete search history.

(56) References Cited

U.S. PATENT DOCUMENTS

| | | | |
|---|---|---|---|
| 4,662,885 A | | 5/1987 | DiPisa, Jr. |
| 4,727,873 A | | 3/1988 | Mobin-Uddin |
| 5,108,419 A | | 4/1992 | Reger et al. |
| 5,882,329 A | * | 3/1999 | Patterson ............ A61B 17/3207 604/500 |
| 6,203,561 B1 | | 3/2001 | Ramee et al. |
| 6,458,139 B1 | * | 10/2002 | Palmer ................. A61B 17/221 606/113 |
| 6,544,279 B1 | * | 4/2003 | Hopkins ................... A61F 2/01 606/194 |
| 6,733,521 B2 | * | 5/2004 | Chobotov ................ A61F 2/07 606/108 |
| 7,306,618 B2 | | 12/2007 | Demond et al. |
| 7,323,001 B2 | * | 1/2008 | Clubb ...................... A61F 2/01 606/200 |
| 7,875,050 B2 | | 1/2011 | Samson et al. |
| 2007/0088383 A1 | * | 4/2007 | Pal ......................... A61F 2/013 606/200 |

* cited by examiner

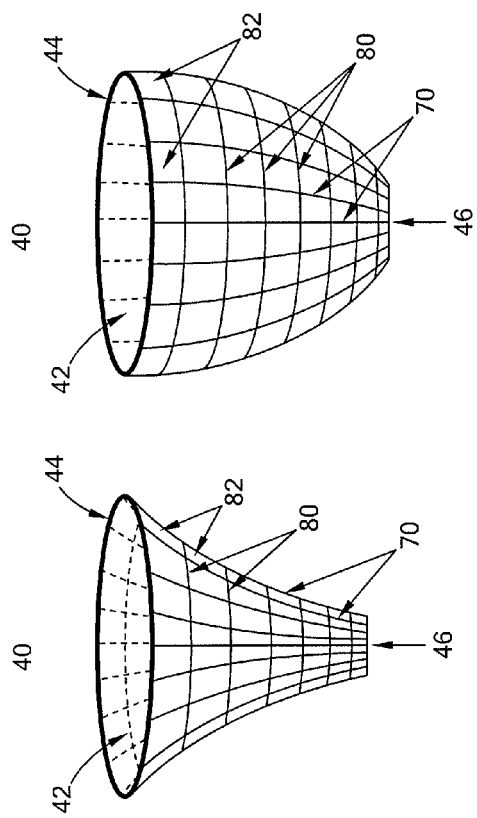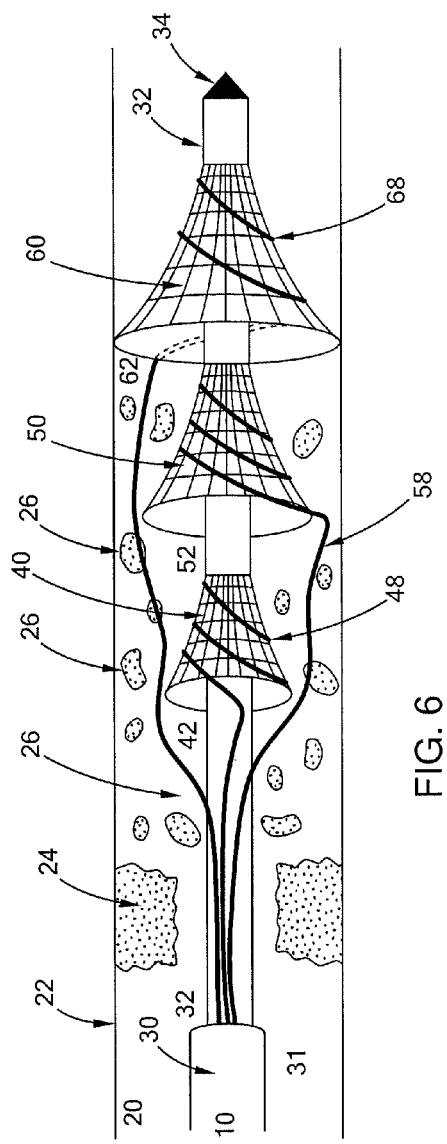

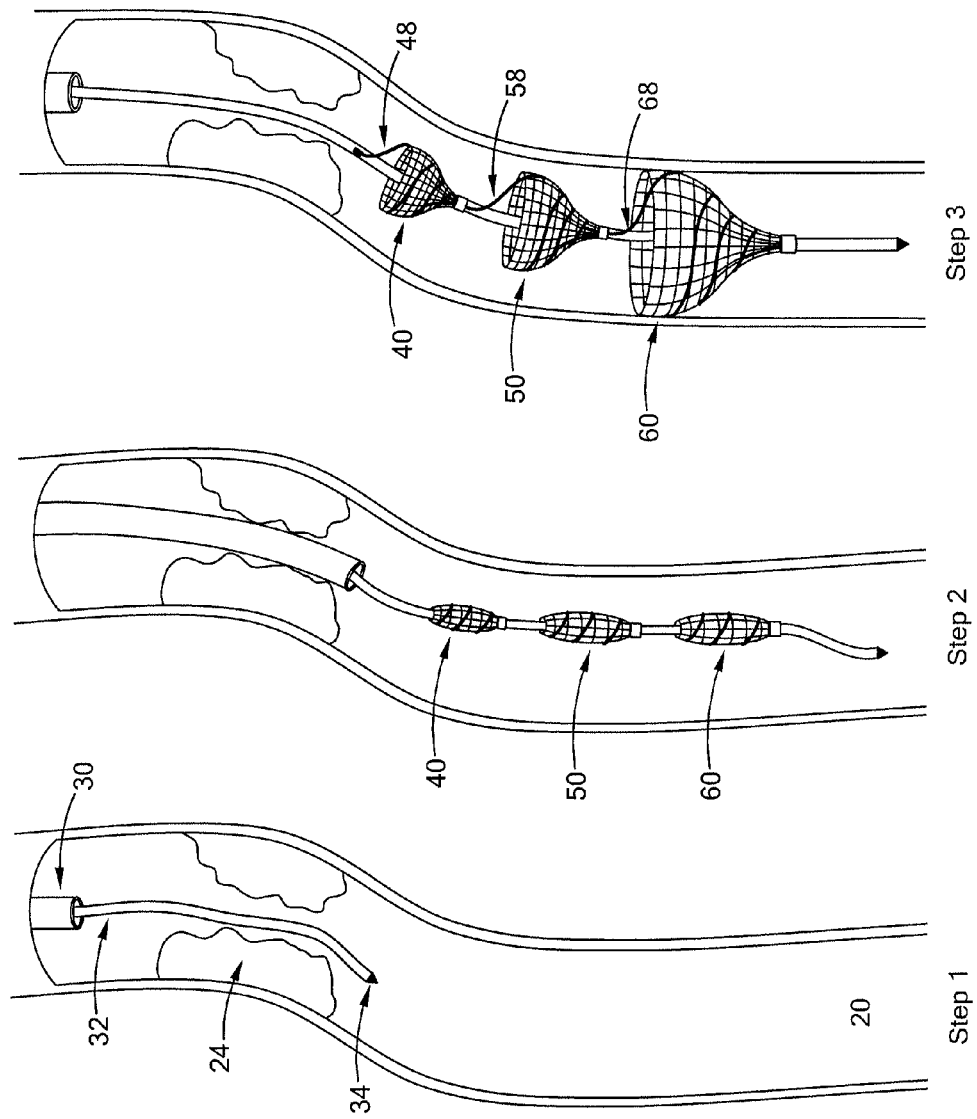

SHAPE MEMORY METAL EMBOLI TRAP

CROSS-REFERENCE TO RELATED APPLICATIONS

This application claims the benefit of U.S. Provisional Application No. 61/788,549 filed on Mar. 15, 2013, entitled "NITINOL EMBOLI TRAP," the entire contents of which are incorporated herein by reference.

BACKGROUND

The present invention relates generally to medical devices. More specifically, the invention relates to intravascular embolus trap devices.

Embolus trap devices are percutaneously placed in a body vessel to prevent emboli from traveling and creating an undesirable embolism, e.g., pulmonary embolism. For example, vena cava filters are used for trapping emboli in the vena cava filter to prevent pulmonary embolism. Also, anti-platelet agents and anticoagulants may be used to breakdown blood clots. Moreover, snares and baskets (e.g., stone retrieval baskets) are used for retrieving urinary calculi. Additionally, occlusion coils are commonly used to occlude aneurysms and accumulate thrombi in a body vessel. Treatments for a stenotic lesion the potential effect of releasing blood clots and other thrombi plaque in the vasculature of the patient.

During stenosis treatments, there is a risk of such blood clots and thrombi being undesirably released into the blood flow within the vasculature. Therefore, embolus trap devices, such as occlusion devices and filters, have been developed to collect blood clots and thrombi. However, currently known devices may be improved to secure blood clots and thrombi during removal of the embolus trap device.

SUMMARY

There is a need to improve embolus trap devices in order to better secure blood clots and thrombi during extraction from the body vessel. In one aspect of the present invention, an embolus trap device for deployment in a body vessel is provided for filtering emboli within the body vessel. The embolus trap device generally includes a plurality of filter baskets having openings formed therethrough and basket collapse wires configured to the external surface of each filter basket. The basket collapse wire can be pulled and released by the medical practitioner so as to allow the filter to be moved between a collapsed state for delivery or withdrawal and an expanded state to collect the emboli. Additionally, the basket collapse wire is disposed about at least a portion of the filter when in the extraction position so as to close the filter basket into a collapsed state, to secure the collected emboli. The collapsed state permits the embolus trap device to be extracted from the body vessel.

In another aspect, the embolus trap device includes a first filter basket and a second filter basket positioned distal to the first filter basket. The first filter basket has a mouth portion with a diameter smaller than the mouth portion of the second filter basket. The filter baskets define a plurality of openings which may be of identical size between the filter baskets or may differ from one another. The embolus trap device may also include a third filter basket spaced apart from the first and the second filter elements, and may include more filter baskets than even three, so long as the mouth portion of the most distal filter basket has the largest diameter of all the filter baskets.

In another aspect of the present invention, the embolus trap device includes a delivery sleeve that is movable with respect to the filter baskets between a delivery position and a non-delivery position. The delivery sleeve is disposed about at least a portion of the filter baskets when in the delivery position so that the filter is in a collapsed state for delivery of the embolus trap device within the body vessel. Additionally, the delivery sleeve is located distal to the filter when in the non-delivery position so as to allow the filter to open into an expanded state and facilitate collection of the emboli. The embolus trap device may also include a sleeve release wire coupled with the delivery sleeve and to control the position thereof.

In another aspect of the present invention, an assembly for removing emboli from a body vessel is provided. The assembly generally includes an inflatable catheter having an expanded state for expanding narrowed or restricted portions of the body vessel, an outer catheter having an interior lumen for delivering the inflatable catheter into the body vessel, and an embolus trap device positioned distal to the inflatable catheter for collecting emboli that are potentially dislodged during expansion of the body vessel.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 4 is a side view of a filter basket of the present device;

FIG. 5 is a side view of a different embodiment of a filter basket of the present device;

FIG. 6 is an environmental side view of an embolus trap device in an expanded state in the process of collecting embolus fragments from the blood stream in accordance with one embodiment of the present invention;

FIG. 8 is an environmental side view of the embolus trap device from FIG. 6 depicted in the steps of introduction to and expansion within a body vessel.

DETAILED DESCRIPTION

Embodiments of the present invention generally provide embolus trap devices, embolus collection apparatus, and methods for capturing emboli in a body vessel. One particular procedure in which embolus capture may be necessary is during angioplasty for treatment of a stenosis, particularly a carotid artery stenosis. The embodiments provide a method for ensuring capture of many embolus fragments in ways that have not been possible with devices of previous designs.

Throughout this description, it will be understood that, as is known in the art, the term "proximal" refers to the portion of the embolus trap device that is closest to the medical professional and the term "distal" refers to the opposing portion of the embolus trap device, which is positioned within the body vessel.

Figure 1:
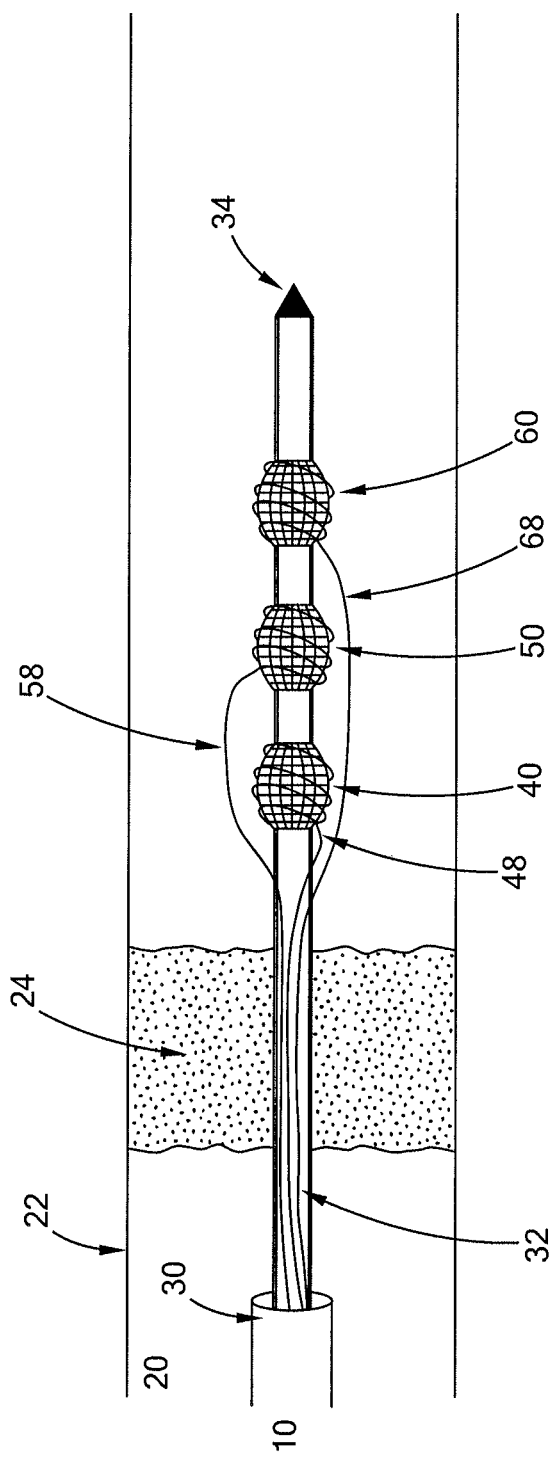
FIG. 1 is an environmental side view of an embolus trap device in a collapsed state for delivery within or extraction from a blood vessel in accordance with one embodiment of the present invention.

Referring now to the drawings, FIG. 1 shows an embolus trap device 10 to be positioned within a body vessel, such as a blood vessel 20, in its collapsed form. Here, the embolus trap device has been deployed in blood vessel 20 percutaneously and through the embolus 24. Embolus 24 may be blood clots, plaque fragments, or any other biological matter capable of occluding a body vessel. Deployment has been assisted by embolus disruption tip 34, which in the illustrated embodiment is cone shaped and is located at the extreme distal end of the embolus trap device 10. Embolus disruption tip 34 may be formed in a variety of shapes and can be blunted or rounded. It is preferably made of metal which is capable of penetrating an embolus 24, such as stainless steel, however other materials such as hard plastics or other metals are also candidate materials for its construction.

Continuing with FIG. 1, the device assembly includes a dual-catheter assembly consisting of outer catheter 30 and inner catheter 32. In one embodiment, inner catheter 32 is an inflatable catheter suitable for angioplasty or other related stenotic treatments. The inner catheter 32 may be assisted through the vasculature by means of a wire guide (not illustrated.)

The embolus trap device 10 includes a plurality of filter baskets; as illustrated, the device 10 has three filter baskets 40, 50 and 60, but other embodiments may have two filter baskets, and yet other embodiments may have four or more filter baskets. The filter baskets 40, 50, and 60 are positioned downstream of embolus 24 to trap and prevent the downstream travel of fragments formed therefrom and reduce the likelihood of downstream blood vessels becoming blocked. The filter baskets 40, 50, and 60 are encircled by a mesh 80 which may be a weave having openings that permit blood to flow therethrough but that prevent downstream migration of emboli 24.

The filter baskets 40, 50, and 60 each preferably include an open, proximally-located lip portion 44, 54, and 64 respectively, that selectively expand to receive the emboli 24 and a closed, distally-located base portions 46, 56, and 66 to collect and/or store the emboli 24. The lip portions 44, 54, 64 are movable so that the embolus trap device 10 defines a collapsed state (FIG. 1) and an expanded state (FIG. 6). When in the expanded state, the device 10 is able to collect and trap emboli 24 within the respective filter baskets 40, 50, and 60, while the device when in the collapsed state is able to be inserted and withdrawn from the blood vessel 20, as will be discussed in more detail below.

Continuing with FIG. 1, embolus trap device 10 additionally preferably includes a collapse wire for each filter basket present. In the illustrated embodiment, collapse wires 48, 58, and 68 are respectively attached to filter baskets 40, 50, and 60. The collapse wires may be made of any suitable material or combination of materials that are biocompatible or capable of being made biocompatible, such as stainless steel, other biologically compatible metals, polymers, plastics, alloys (including super-elastic alloys), or composite materials. In the illustrated embodiment, the collapse wires are wound from the distal base portions 46, 56, 66 of filter baskets 40, 50, 60, to the lip 44, 54, 64 before following the length of inner catheter 32 and extending through the proximal end of the device 10 where they can be manipulated by the practitioner. The filter baskets 40, 50, 60 are fixedly attached to inner catheter 32 at basket fixture points by their distal base portions 46, 56, 66, in some embodiments by soldering or welding. To assist in identification of which collapse wire controls which filter basket, the collapse wires may be of different lengths, thicknesses, or may be color- or texture-coded, or all of the above. For reasons described below it will become apparent that a practitioner will know which collapse wire corresponds to which filter basket.

Figure 2:
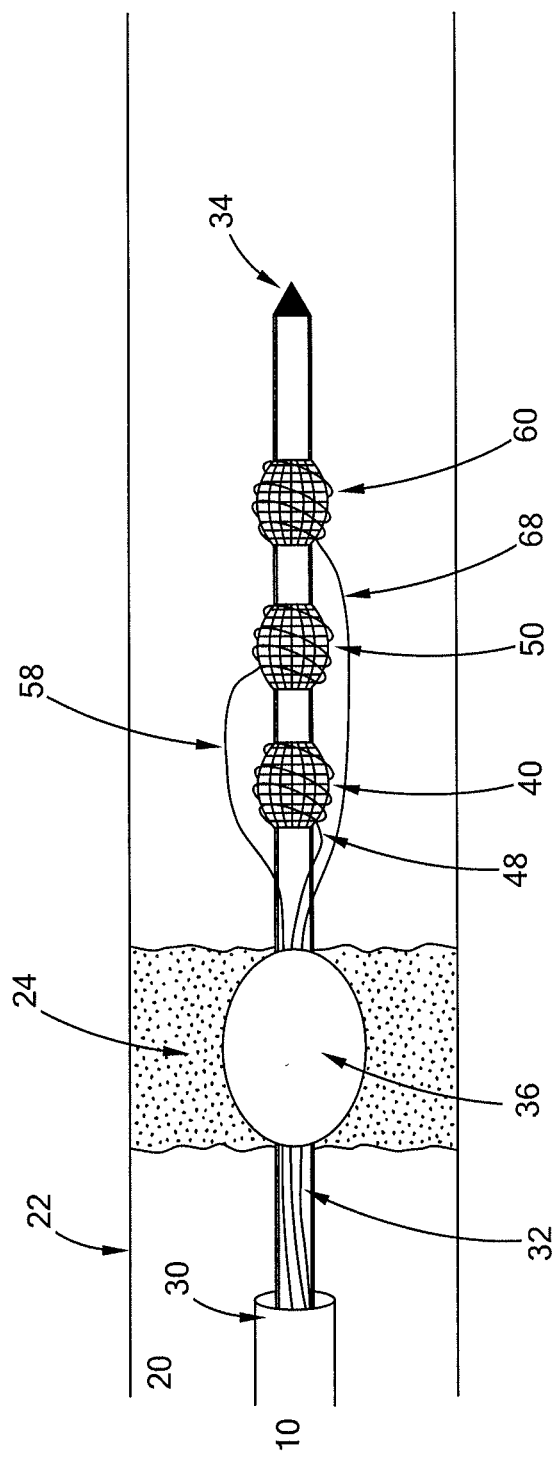
FIG. 2 is an environmental side view of an embolus trap device in a collapsed state including an optional balloon such as for angioplasty, the balloon being depicted in its expanded state.

Turning now to FIG. 2, an alternate embodiment of embolus trap device 10 is shown. In this embodiment, an optional expandable angioplasty balloon 36 is shown. The expandable balloon 36 is preferably expanded by a fluid, such as water or saline solution as is well known in the art. Controlled inflation of balloon 36 leads to expansion of the body vessel 20, which in turn can potentially cause the release of emboli 24 into the blood stream, which are captured by the filter baskets 40, 50, and 60.

Figure 3:
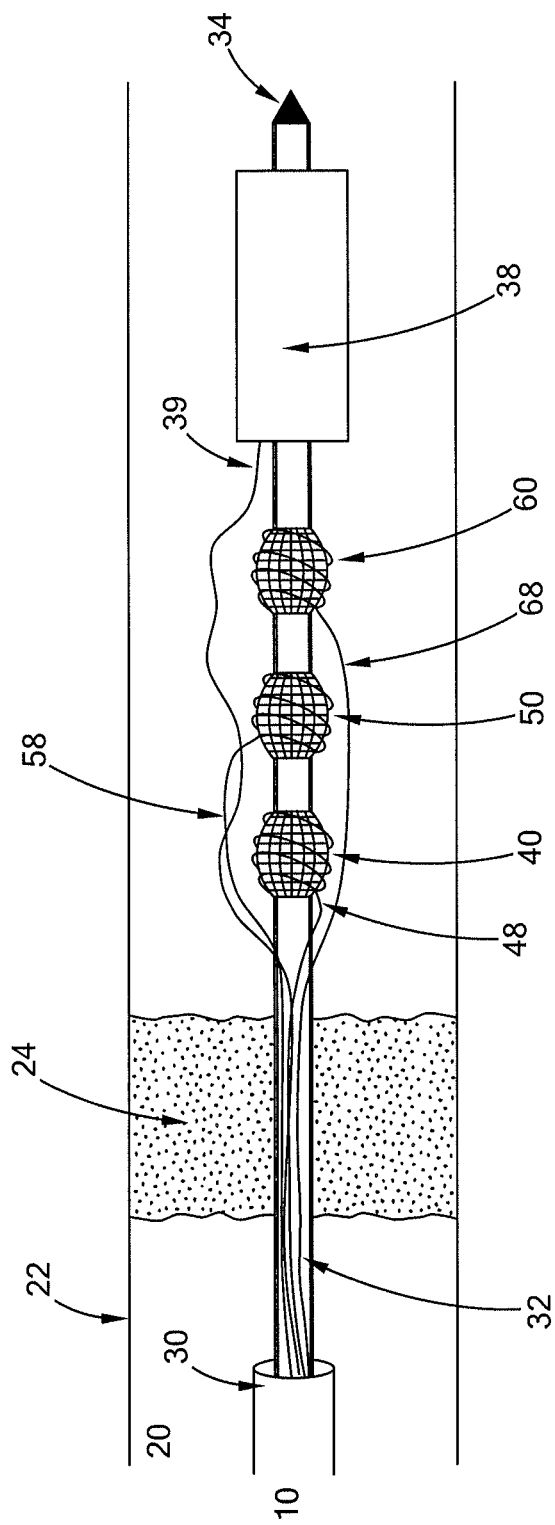
FIG. 3 is an environmental side view of an embolus trap device in a collapsed state including an optional delivery sleeve and sleeve release wire.

Yet another embodiment of embolus trap device 10 is shown in FIG. 3. In this case, delivery sleeve 38 is illustrated. The function of delivery sleeve 38 is to assist in keeping the filter baskets 40, 50, 60 in their collapsed configurations during deployment into vessel 20. When the device 10 has been positioned in vessel 20 as desired, the practitioner then uses sleeve release wire 39 to move the delivery sleeve clear of filter baskets 40, 50, 60. In the illustrated embodiment, the delivery sleeve 38 distal to the filter baskets 40, 50, and 60, although an unillustrated design in which the delivery sleeve 38 is moved proximal to the filter baskets is also envisioned. It should be noted that the filter baskets 40, 50, 60 are still constrained by their respective collapse wires 48, 58, 68, and that full expansion of a device 10 having a delivery sleeve 38 will also require loosening of the collapse wires.

Delivery sleeve 38 can be a hollow tube made of any suitable material, such as mesh/net cloth, nylon, polymeric material, Teflon, or a woven mixture of any of the above materials. The delivery sleeves 38 is preferably radially flexible enough so as to negotiate the winding paths of the blood vessel 20, but is preferably not radially flexible enough so that is substantially radially expands when disposed around the filter baskets 40, 50, 60.

Continuing with FIGS. 1-3, the layout of filter baskets 40, 50, 60 along the length of device 10 are described. The filter baskets 40, 50, 60 have lips 44, 54, 64 which define mouth portions 42, 52, 62, respectively. The diameters of mouth portions 42, 52, 62 generally increase the closer each filter basket 40, 50, 60 is to the distal end of device 10. This design introduces a redundancy in embolus capture to the device; embolic fragments 26 that do not follow the flow of liquid in the vessel 20 through the interior of proximal basket 40 may be caught by middle basket 50, or will be caught by distal filter basket 60. In a preferred embodiment, the diameter of mouth 62 of filter basket 60 is expanded to match the inner diameter of vessel 20 such that lip 64 forms a tight seal with the vessel, ensuring that all embolic fragments 26 that are not captured by filter baskets 40 or 50 will remain within filter basket 60.

In certain situations, it may be advantageous for various portions of embolus trap device 10 to be coated with reconstituted or naturally-derived bioresorbable or bioremodelable collagenous materials such as extracellular matrices (ECMs). ECMs such as submucosa, renal capsule membrane, dermal collagen, dura mater, pericardium, fascia lata, serosa, peritoneum or basement membrane layers, including liver basement membrane may be employed as coatings of portions or all of the exteriors of components that contact the inner vessel wall 22 of vessel 20, such as distal filter basket 60, outer catheter 30, or any other portion desired. ECMs may retain molecules such as growth factors or angiogenic materials native to the contexts from which they were prepared which may be desirable for ensuring the health of the vessel after treatment.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like.

In this embodiment, the submucosa or other ECM material is used to temporarily adhere the filter 26 to the walls of a body vessel in which the embolus trap device 10 is deployed. As discussed above, the submucosa or other ECM material has a natural adherence or wettability to body fluids and connective cells comprising the connective tissue of a body vessel wall. Due to the temporary nature of the duration in which the embolus trap device 10 is deployed in the body vessel, host cells of the wall will adhere to the filter basket 60 but not differentiate, allowing for retrieval of the embolus trap device 10 from the vessel 20.

Turning now to FIGS. 4 and 5, two embodiments of filter baskets 40, 50, 60 are illustrated. The filter basket 40, 50, 60, when in the expanded state, preferably has a generally decreasing radius such that a first cross-sectional area of the filter 26 taken along a plane adjacent to the lip portion 44, 54, 64 is substantially larger than a second cross-sectional area of the filter 40, 50, 60 taken along a second plane adjacent to the base portion 46, 56, 66. For example, in FIG. 4 the expanded state is preferably generally cone-shaped such as to have a constantly decreasing radius along a longitudinal axis, whereas in FIG. 5 the expanded state is generally cup-shaped such that the radius is constant for a portion of the filter basket and then decreases more sharply closer to the distal base portion.

Each of the filter baskets 40, 50, 60 preferably includes a plurality of struts 70 (FIGS. 4 and 5) for supporting the filter mesh 80. The struts 70 extend from the base portion 46, 56, 66 to the lip portion 44, 54, 64 of each of the filter baskets 40, 50, 60 and are generally circumferentially evenly-spaced from each other at the lip portion 44, 54, 64. In one embodiment, the struts 70 are secured to an inner surface of the filter mesh 80 such that the filter mesh 80 and the struts 70 collapse and expand in unison. In another embodiment, the filter mesh 80 is woven or otherwise composed around the framework provided by the plurality of struts 70.

The struts 70 may be comprised of any suitable material such as a superelastic material, stainless steel wire, cobalt-chromium-nickel-molybdenum-iron alloy, or cobalt-chrome alloy. It is understood that the struts 38 may be formed of any other suitable material, such as shape memory alloys. Shape memory alloys have the desirable property of returning to a remembered state when heated above a transition temperature. A shape memory alloy suitable for the present invention is a mixture of Nickel and Titanium available under the more commonly known name NITINOL. When this material is heated above the transition temperature, the material undergoes a phase transformation from martensite to austenic, such that material returns to its remembered state. The transition temperature is dependent on the relative proportions of the alloying elements Nickel and Titanium and the optional inclusion of alloying additives.

In one embodiment, the struts 70 are made from NITINOL with a transition temperature that is slightly below normal body temperature of humans, which is about 98.6 degrees Fahrenheit. Therefore, when the device 10 is deployed in the blood vessel 20 and exposed to normal body temperature, the alloy of the struts 70 will transform to the remembered austenite state, which for one embodiment of the present invention is the expanded configuration when the filter baskets 40, 50, 60 are deployed in the blood vessel 20, as will be discussed in more detail below.

In a preferred embodiment, the mesh 80 is made of NITINOL and is integral with the assembly of struts 70. The means of making the mesh integral with the struts can be done by interposing the struts through the openings of the mesh, weaving the mesh about the strut assembly, welding or soldering the mesh at a variety of points to the surfaces of the struts, tying the mesh about the struts, or so forth. The mesh 80 may itself be made of woven NITINOL. In other embodiments, the mesh 80 may also or alternatively be made of a net cloth, nylon, polymeric material, Teflon, or woven mixtures thereof without falling beyond the scope or spirit of the present invention. In yet other embodiments, a filter basket 40, 50, 60 which is made of NITINOL may be integrated with another material either on the interior or the exterior, such as net cloth, nylon, Teflon, et cetera.

Struts 70 are also preferably able to be radially collapsed. Such a property allows for higher degrees of adaptability in both deployment and extraction of the device 10. Notably, the flexibility of struts 70 will allow for collapse around masses of collected emboli so that they can be retained by the mesh 80. Struts 70 must be able to be flexible enough to encompass the collected emboli and contract to the removal configuration.

The openings 82 defined by the mesh 80 are preferably configured such as to effectively promote blood flow through the filter baskets 40, 50, 60 while still being small enough to retain embolic fragments 26 as collection continues. Because blood flow is physiologically crucial and is also responsible for helping to dislodge and promote the movement of embolic fragments 26, embolus trap device 10 must not completely impede it. The openings 82 may be of substantially similar sizes in all filter baskets 40, 50, 60, or they can decrease in size in the distal direction such that they are substantially smaller in each basket when progressing from the proximal to the distal end, recognizing that the purpose of distal filter baskets is to catch and trap embolic fragments 26 that are missed by the more proximal filter baskets.

In addition to maximizing the trapping volume of and minimizing the flow losses through, the filter baskets 40, 50, 60 are designed to maximize the radial expansion of the embolus trap device 10. The lip portions 44, 54, 64 can comprise a single loop of shape memory alloy biased into its expanded state, allowing it the mouth portions 42, 52, 62 to expand to their maximum size after release of the collapse wires 48, 58, 68. In particular, the most distal filter basket 60 has its lip portion 64 configured to effectively form a seal between the filter basket 60 and the blood vessel 20 and thus prevent emboli 26 from flowing past the filter 60.

FIG. 6 shows an embolus trap device 10 configured in its expanded position in the process of trapping embolus fragments 26. The filter baskets 40, 50, 60 are configured such as to collect embolus fragments 26 of varying sizes and shapes and in different positions radially within blood vessel 20. For example, the first filter basket 40 comprises a relatively small mouth portion 42 which only permits emboli which are moving in the central portion of vessel 20 to be trapped. Those that are flowing closer to the vessel wall 22 may be captured by middle filter basket 50 or distal filter basket 60.

Varying the mesh 80 and size of the openings 82 across the filter baskets 40, 50, 60 also impacts the size of embolic fragments 26 that can be collected. For instance, assuming the openings 82 of the mesh 80 enclosing filter basket 40 are largest, of distal filter basket 60 are the smallest, and the second filter basket 50 having intermediate openings, relatively large emboli will be trapped by filter basket 40, allowing medium-sized emboli to flow through to middle basket 50, and relatively small emboli will be collected by the third filter basket 60. Because even distal filter basket 60 has openings 82 in its meshwork 80, harmless particles such as blood cells are permitted to flow therethrough.

Alternatively, substantially similar meshworks 80 may be used for every filter basket fixedly attached to device 10. In this case, the radial flow position, rather than the size, of the embolic fragments 26 will dictate which filter basket collects the embolic fragments. In this embodiment, it is still favored to include a meshwork 80 with the smallest openings 82 on distal filter basket 60, as this will be the last potential capture point for the smallest embolic fragments 26 that the device may need to collect. Emboli not collected in distal filter basket 60 will simply remain in the vasculature, and if the mesh 80 of filter basket 60 is not fine enough, undesirable clots and clogs may occur downstream of device 10.

In an embodiment in which the mouth portion 42 of filter basket 40 has a diameter 50% of the diameter of vessel 20, and mouth portion 52 of filter basket 50 has 75%, and mouth portion 62 of filter basket 60 has a diameter equal to that of the vessel 20 (forming a tight seal around which emboli 26 cannot flow), assuming an equal radial distribution of fragments, the filter baskets will fill in order from proximal to distal ends. A problem in single-basket embolic trap devices is that closure of nearly-full, full, or overfilled baskets leads to spill out of embolic fragments 26 into the blood stream, thereby causing the undesired downstream flow of particles that the device was intended to protect against in the first place.

Withdrawal of embolus trap device 10 from body vessel 20 is an important procedure. A function of this invention is to maximize the capture of embolic fragments that are traveling downstream through the vasculature; as such, the preferred order of basket closure is from the proximal end to the distal end.

Figure 7:
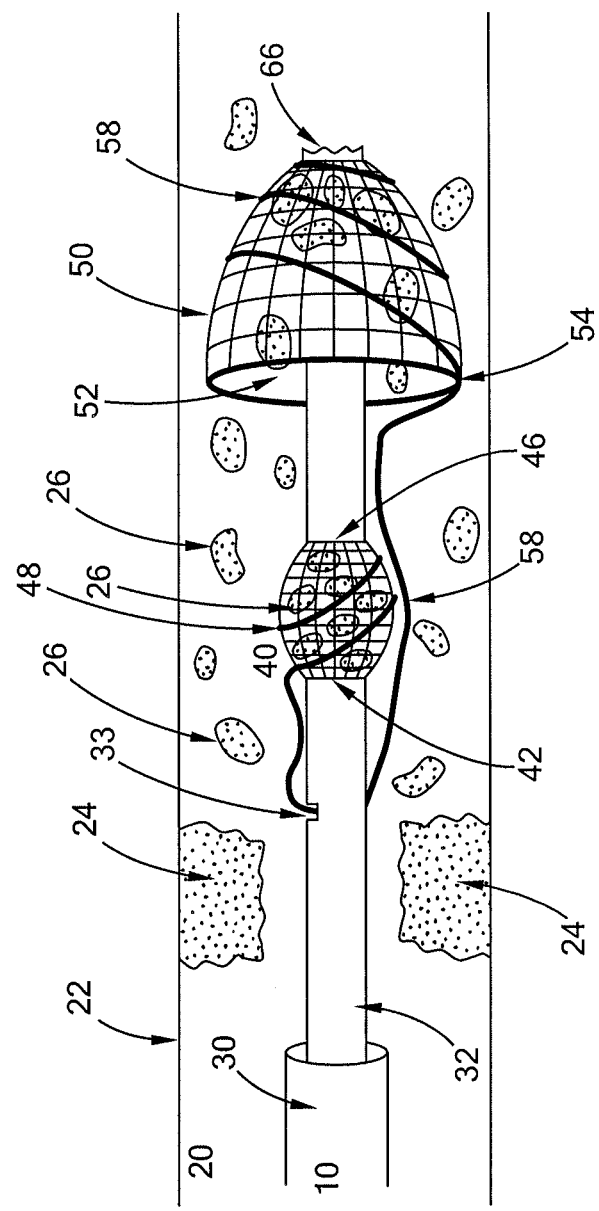
FIG. 7 is an environmental side view of the embolus trap device collecting embolus fragments from the blood stream with one filter basket filled with embolus fragments in the collapsed state and a distal filter basket in the expanded state.

FIG. 7 depicts a portion of an embolus trap device 10 that is in the process of being collapsed prior to removal of the device from the patient. Proximal filter basket 40 is filled with embolic fragments and has been closed. The practitioner has pulled collapse wire 48 taut through wire retraction slot 33 and caused the wire, which is wrapped around the outside surface filter basket 40 in a spiral configuration, to close the filter basket 40 radially, trapping the embolic fragments inside. Filter basket 50, located distal to filter basket 40, is still expanded and catching embolic fragments, will be closed next. Finally, the most distal filter basket 60 which is not depicted will be closed and the entire assembly can then be extracted.

The collapse wires 48, 58, 68 have been illustrated through this description have been shown as being wrapped preferably but not necessarily spirally around the exterior of filter baskets 40, 50, 60, respectively. To prevent slippage of the collapse wire and ensure closure of the filter baskets, it may be necessary to somehow integrate the collapse wires into the filter baskets, such as by interweaving the collapse wires with the meshwork, thereby having portions of the collapse wire in the interior of the filter baskets and other portions on the exterior. Alternatively, it may be advantageous in certain embodiments to create a series of closed loops on the exterior of the filter baskets 40, 50, 60 through which the collapse wires 48, 58, 68 will be passed in order to keep the collapse wires in contact with the exterior of the basket. In yet another embodiment, the collapse wires can be placed between two layers of meshwork and where the collapse wires sit in between these two, a channel will be formed therethrough, allowing the collapse wires to remain in place on their respective filter baskets.

It will be appreciated that other configurations of collapse wires can be substituted so long as they provide a means of closing off the filter baskets 40, 50, 60. For instance, in one such alternative embodiment, the distal ends of the collapse wires might terminate in fairly rigid closed loops which would surround the distal portions of the filter baskets when in an expanded state. Because of their rigidity, the closed loops would not change their size or shape, and so when retracted distally due to the practitioner pulling on the collapse wires, the filter baskets would be drawn shut as the closed loops passed over them.

FIG. 8 illustrates deployment of the device into the vessel. Although a number of intermediate steps may be possible, for illustrative purposes this procedure has been distilled into three major steps. In the first step, the outer catheter 30 has been introduced to vessel 20 percutaneously. Inner catheter 32 has been pushed out of the inner lumen of outer catheter 30, and embolus disruption tip 34 has been used to break through embolus 24. Step two shows further feeding of inner catheter 32 through outer catheter 30 such that filter baskets 40, 50, 60 are now disposed distal to the embolus 24 within vessel 20. The filter baskets 40, 50, 60 are still in their collapsed states, constrained by collapse wires 48, 58, 68.

In step three of FIG. 8, the practitioner has caused filter baskets 40, 50, 60 to adopt their expanded configurations by slackening collapse wires 48, 58, and 68. The memory metal of the filter baskets is biased into the expanded configuration and the physical force of the collapse wires holding them shut is the only thing preventing expansion in this embodiment. Note that distal filter basket 60 in this embodiment forms a tight seal inside of vessel 20. In fact, the preferred order of basket expansion during deployment is 60 first, then 50, then 40, in case the process of deploying the device has caused a large number of embolic fragments to dislodge from the embolus 24. Because distal filter basket 60 has the largest maximum diameter and is likely to be covered by the finest mesh, it is the best basket to expand first, with the smaller baskets following.

It is intended that the foregoing detailed description be regarded as illustrative rather than limiting, and that it be understood that it is the following claims, including all equivalents, that are intended to define the spirit and scope of this invention.

What is claimed is:

1. An embolus trap device having a proximal end and a distal end comprising:
    an outer catheter having an interior lumen;
    an inner catheter disposed within the interior lumen of the outer catheter;
    a plurality of basket fixture points spaced along a length of the inner catheter;
    a plurality of filter baskets disposed at the basket fixture points of the inner catheter, the filter baskets comprising a plurality of struts and a mesh disposed about the plurality of struts, the mesh having a plurality of openings formed therethrough, the filter baskets having a closeable mouth portion having an inner diameter, the filter baskets being placed at the basket fixture points in order of increasing size of the inner diameter of the mouth portions from the proximal end to the distal end of the embolus trap device;
    and a plurality of collapse wires, each of the collapse wires being fixedly attached at a distal end of the collapse wire to a distal end of one of the filter baskets.

2. The embolus trap device of claim 1 further comprising an embolus disruption tip.

3. The embolus trap device of claim 2 in which the collapse wires conform the device to a collapsed state when pulled and conform the device to an expanded state when slackened, the collapse wires being operable independent of each other.

4. The embolus trap device of claim 3 in which the collapse wires are identifiably marked so that it is clear which basket each operates and that the inner catheter has at least one wire retraction slot, through which a proximal portion of at least one of the collapse wires is guided into the inner catheter, the at least one wire retraction slot being proximal from the filter, to which the at least one of the collapse wires is attached.

5. The embolus trap device of claim 4 in which the struts of the filter baskets are made of a shape memory alloy having a remembered state.

6. The embolus trap device of claim 5 in which the remembered state of the shape memory alloy is the expanded state.

7. The embolus trap device of claim 6 wherein the shape memory alloy is NITINOL.

8. The embolus trap device of claim 7 further comprising an inflatable balloon portion.

9. The embolus trap device of claim 7 further comprising a delivery sleeve movable with respect to the filter baskets between a delivery position and a non-delivery position, the delivery position comprising the sleeve being disposed about at least a portion of the filter baskets so that the filter is in a collapsed state, and the delivery sleeve being located distal to the filter when in the non-delivery position so as to allow the filter to open into an expanded state.

10. The embolus trap device of claim 9 further comprising a sleeve release wire coupled with the delivery sleeve to control the position thereof.

11. The embolus trap device of claim 7 wherein the openings formed through the mesh are substantially the same size across all filter baskets.

12. The embolus trap device of claim 7 in which the mesh is integral with the struts.

13. The embolus trap device of claim 12 in which the mesh and struts comprise woven NITINOL.

14. The embolus trap device of claim 7 wherein the openings formed through the mesh are substantially smaller in each basket than the openings formed through the mesh of the basket proximal to it.

15. A method of collecting embolic debris comprising:
    providing an embolus trap device having a proximal and a distal end comprising:
        an outer catheter having an interior lumen;
        an inner catheter disposed within the interior lumen of the outer catheter;
        a plurality of basket fixture points along length of the inner catheter;
        a plurality of filter baskets disposed at the basket fixture points of the inner catheter, the filter baskets comprising a plurality of struts and a mesh disposed about the plurality of struts, the mesh having a plurality of openings formed therethrough, the filter baskets having a closeable mouth portion having an inner diameter, the filter baskets being placed at the basket fixture points in order of increasing size of the inner diameter of the mouth portions from the proximal to the distal end of the embolus trap device;
        and a plurality of collapse wires, one of the plurality of collapse wires being attached to each of the filter baskets and having a distal end fixedly attached to the filter basket at a distal base portion of the filter basket;
    deploying the embolus trap device percutaneously into a vessel or cavity of a patient's body;
    moving the inner catheter through the embolic mass;
    opening the plurality of filter baskets to deploy the device in its expanded state;
    filling the filter baskets with debris as the embolus disintegrates;
    closing the filter baskets by the collapse wires to return the device to its collapsed state; and
    retracting the embolus trap device from the patient's body.

16. The method of claim 15 wherein the step of closing comprises sequentially closing the filter baskets relative to the basket fixture points, wherein the filter basket disposed on the most proximal basket fixture is closed first.

17. An embolus trap device having a proximal and a distal end comprising:
    an outer catheter having an interior lumen;
    an inner catheter disposed within the interior lumen of the outer catheter and having a breakage cone at its distal end;
    a plurality of basket fixture points along length of the inner catheter;
    a plurality of filter baskets having an exterior surface, a closed state and an expanded state, and comprising a body portion made of woven NITINOL and a closeable mouth portion having an inner diameter comprising a NITINOL ring, the filter baskets being placed at the basket fixture points in order of increasing size of the inner diameter of the mouth portions from the proximal to the distal end of the embolic protection device;
    and a plurality of collapse wires disposed about the exterior surfaces of the filter baskets in both the closed state and the expanded state, the collapse wires being configured to constrict the filter baskets when pulled toward the proximal end of the embolic protection device.

* * * * *